(12) United States Patent
Jan

(10) Patent No.: US 8,759,597 B2
(45) Date of Patent: Jun. 24, 2014

(54) METHODS FOR PRODUCING ZEOLITE CATALYSTS AND METHODS FOR PRODUCING ALKYLATED AROMATIC COMPOUNDS USING THE ZEOLITE CATALYSTS

(75) Inventor: Deng-Yang Y. Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 94 days.

(21) Appl. No.: 13/450,296

(22) Filed: Apr. 18, 2012

(65) Prior Publication Data

US 2013/0281754 A1 Oct. 24, 2013

(51) Int. Cl.
*C07C 2/66* (2006.01)

(52) U.S. Cl.
USPC .......................................................... 585/467

(58) Field of Classification Search
CPC ................................ C07C 2/66; B01J 29/7038
USPC .......................................................... 585/467
See application file for complete search history.

(56) References Cited

U.S. PATENT DOCUMENTS

| | | | |
|---|---|---|---|
| 5,869,417 A | 2/1999 | Woo et al. | |
| 5,907,073 A * | 5/1999 | Ghosh ............................ | 585/467 |
| 6,297,417 B1 | 10/2001 | Samson et al. | |
| 6,500,996 B1 | 12/2002 | Brown et al. | |
| 6,608,232 B1 | 8/2003 | Jacquot et al. | |
| 6,680,013 B1 | 1/2004 | Stein et al. | |
| 7,326,401 B2 | 2/2008 | Tatsumi et al. | |
| 7,663,011 B2 | 2/2010 | Shan et al. | |
| 7,731,839 B2 | 6/2010 | Brown et al. | |
| 2007/0202038 A1 | 8/2007 | Yaghi et al. | |
| 2009/0054670 A1 | 2/2009 | Kawabata et al. | |
| 2009/0325785 A1 | 12/2009 | Moscoso et al. | |
| 2010/0132549 A1 | 6/2010 | Yaghi et al. | |
| 2010/0197946 A1 | 8/2010 | Mizuno et al. | |
| 2010/0274067 A1 | 10/2010 | Brown et al. | |
| 2010/0298117 A1 * | 11/2010 | Levin et al. ...................... | 502/23 |

FOREIGN PATENT DOCUMENTS

| | | |
|---|---|---|
| EP | 1479663 A1 | 11/2004 |
| RU | 2189859 C2 | 9/2002 |
| WO | 9958243 A2 | 11/1999 |
| WO | 2004056475 A1 | 7/2004 |

OTHER PUBLICATIONS

Silvestre-Albero, J., et al., "Zn-modified MCM-41 as support for Pt catalysts," Applied Catalysis A: General, vol. 351, No. 1, p. 16-23, Dec. 15, 2008.

Sastre, G., et al., "Diffusion of benzene and propylene in MCM-22 zeolite. A molecular dynamics study," Journal of Physical Chemistry B, vol. 103, No. 25, p. 5187-5196, Jun. 24, 1999.

Liu, L, et al., "Synthesis, characterization, and catalytic properties of MWW zeolite with variable Si/Ai ratios," Microporous and Mesoporous Materials, vol. 94, No. 1/3, p. 304-312, Sep. 8, 2006.

Thomas, Catalytic Processes and Proven Catalysts, Academic Press, New York and London, 1970, p. 354.

International Search Report for PCT/US2013/035556, mailing date Aug. 29, 2013.

* cited by examiner

*Primary Examiner* — Thuan D Dang
(74) *Attorney, Agent, or Firm* — Mark R Willis

(57) ABSTRACT

A method for producing a zeolite catalyst includes mixing a zeolite material with a filler material comprising transition phase and alpha alumina, a porosity enhancing agent, and water to produce a paste; mulling the paste; extruding the paste to produce a shaped extrudate; and drying and calcining the shaped extrudate to produce a zeolite catalyst, wherein the zeolite catalyst has a total porosity greater than about 0.60 ml/gm and greater than 15% of a total pore volume of pores in the range from about 550 Å to about 31,000 Å.

16 Claims, 4 Drawing Sheets

METHODS FOR PRODUCING ZEOLITE CATALYSTS AND METHODS FOR PRODUCING ALKYLATED AROMATIC COMPOUNDS USING THE ZEOLITE CATALYSTS

TECHNICAL FIELD

This invention relates generally to methods for producing catalysts used for the alkylation of aromatic compounds and methods for alkylation of aromatic compounds using such catalysts. More particularly, this invention relates to methods for producing zeolite catalysts having improved catalytic activity in diffusion-resistant applications and methods for producing alkylated aromatic compounds using such zeolite catalysts.

BACKGROUND

The alkylation of aromatic hydrocarbons such as benzene with olefins having two, three, or four carbon atoms (hereinafter referred to as "light" olefins), such as ethylene and propylene, is a commercially important process. The production of ethylbenzene is used to provide a feedstock for styrene production, while the alkylation of benzene with propylene produces isopropylbenzene (cumene). Cumene is an important feedstock to make phenol as well as a good gasoline blending component. Numerous other uses exist for such alkylated aromatic hydrocarbons. In these alkylation processes, new catalysts are continuously needed that have a high overall conversion of the feedstock and have a good selectivity of alkylated benzenes.

Zeolite catalysts (hereinafter referred to collectively as "zeolites") have been found to be particularly well-suited for use in the alkylation of aromatic hydrocarbons. Zeolites are crystalline aluminosilicate compositions that are microporous and that are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al, and structure-directing agents such as alkali metals, alkaline earth metals, amines, and/or organoammonium cations. The structure-directing agents reside in the pores of the zeolite and are largely responsible for the particular structure that is ultimately formed. These species balance the framework charge associated with aluminum and can also serve as space fillers. Zeolite catalyst compositions also typically include a filler or binder material mixed with the aluminosilicate material, which helps to form the zeolite catalyst into a desired shape. Zeolites are characterized by having pore openings on the external surface of the catalyst, having a significant ion exchange capacity, and being capable of reversibly desorbing an adsorbed phase, which is dispersed throughout the internal voids of the crystal without significantly displacing any atoms which make up the permanent zeolite crystal structure.

While zeolites have been shown to be useful for the alkylation of a variety of aromatic hydrocarbons with a variety of light olefins, testing has shown that alkylation reactions using zeolite catalysts are highly diffusion limited. The reaction rate is so fast and the diffusion of olefin into and throughout the catalyst to reach all the zeolitic active sites is the rate limiting step. Diffusion within the catalyst depends, in part, on the overall porosity and pore structure of the catalyst and in part on the dispersion of zeolite throughout the matrix. In order to disperse the zeolite throughout the matrix mechanic force through a process such as mulling is applied. However, the compaction invariably reduces the catalyst porosity, increasing the diffusion resistance and thus lowering the catalyst activity.

Accordingly, it is desirable to provide methods for producing zeolite catalysts that have better diffusion characteristics and thus improving the utility of zeolite throughout the entire catalyst. The effect of diffusion resistance on active site utilization and thus catalyst activity is especially evident in the aromatic alkylation with olefin including propylene and ethylene. Furthermore, other desirable features and characteristics will become apparent from the subsequent detailed description and the appended claims, taken in conjunction with the accompanying drawings and the foregoing technical field and background.

BRIEF SUMMARY

Methods for producing zeolite catalysts and methods for producing alkylated aromatic compounds using the zeolite catalysts are disclosed. In an exemplary embodiment, a method for producing a zeolite catalyst includes mixing a zeolite material with a filler material comprising transition phase and alpha alumina, a porosity enhancing agent, and water to produce a paste; mulling the paste; extruding the paste to produce a shaped extrudate; and drying and calcining the shaped extrudate to produce a zeolite catalyst, wherein the zeolite catalyst has a total porosity greater than about 0.60 ml/gm and greater than 15% of a total pore volume of pores in the range from about 550 Å to about 31,000 Å.

In another exemplary embodiment, a method for producing an alkylated benzene compound includes mixing a zeolite material with a filler material comprising transition phase and alpha alumina, a porosity enhancing agent, and water to produce a paste; mulling the paste; extruding the paste to produce a shaped extrudate; drying and calcining the shaped extrudate to produce a zeolite catalyst, wherein the zeolite catalyst has a total porosity greater than about 0.60 ml/gm and greater than 15% of a total pore volume of pores in the range from about 550 Å to about 31,000 Å; and contacting a hydrocarbon stream comprising benzene and an olefin in the presence of the zeolite catalyst.

BRIEF DESCRIPTION OF THE DRAWINGS

The inventive methods will hereinafter be described in conjunction with the following drawing figures, wherein like numerals denote like elements, and wherein.

DETAILED DESCRIPTION

The following detailed description is merely exemplary in nature and is not intended to limit the zeolite catalysts, the application and uses of the zeolite catalysts, or the methods of production of the zeolite catalysts described herein. Furthermore, there is no intention to be bound by any theory presented in the preceding background or the following detailed description.

Alkylbenzenes, such as ethylbenzene and isopropylbenzene, are produced commercially by the reaction of benzene with ethylene and propylene, respectively. The process operates in liquid phase, or at least partially in liquid phase, in order to maintain stable production. The reaction of $C_{2-4}$ olefins with benzene is relatively fast and operates in a reaction region of a catalyst where the diffusion of olefin into the catalyst is the rate limiting step. The rate of the reaction is thereby improved by using a catalyst that allows for a greater diffusion of olefins into the catalyst. The diffusion of olefins into the catalyst is improved by providing a catalyst that has high catalyst porosity, desirable pore structures with the zeolite well-dispersed within the catalyst binder matrix.

As such, the various embodiments contemplated herein relate to methods for producing zeolite catalysts with the zeolite component thereof highly dispersed within the catalyst matrix. In a typical extrusion, method for producing a zeolite catalyst includes optionally milling a stock batch of zeolite to achieve zeolite particles to reduce the aggregate to a specified range of size. As used herein, the term "particle size" means the diameter or average dimension of a particle. Preferably, milling proceeds to a particle size distribution such that greater than about 80%, or for example greater than about 90%, of the milled zeolite particles are in the specified range. Milling can be performed using any known method. In one example, dry- or wet-ball milling may be performed in a tumbler apparatus. In another example, wet milling may be performed by running a zeolite slurry through a chamber containing refractory beads agitated using an impeller as exemplified by Eiger bead mill.

Figure 1:
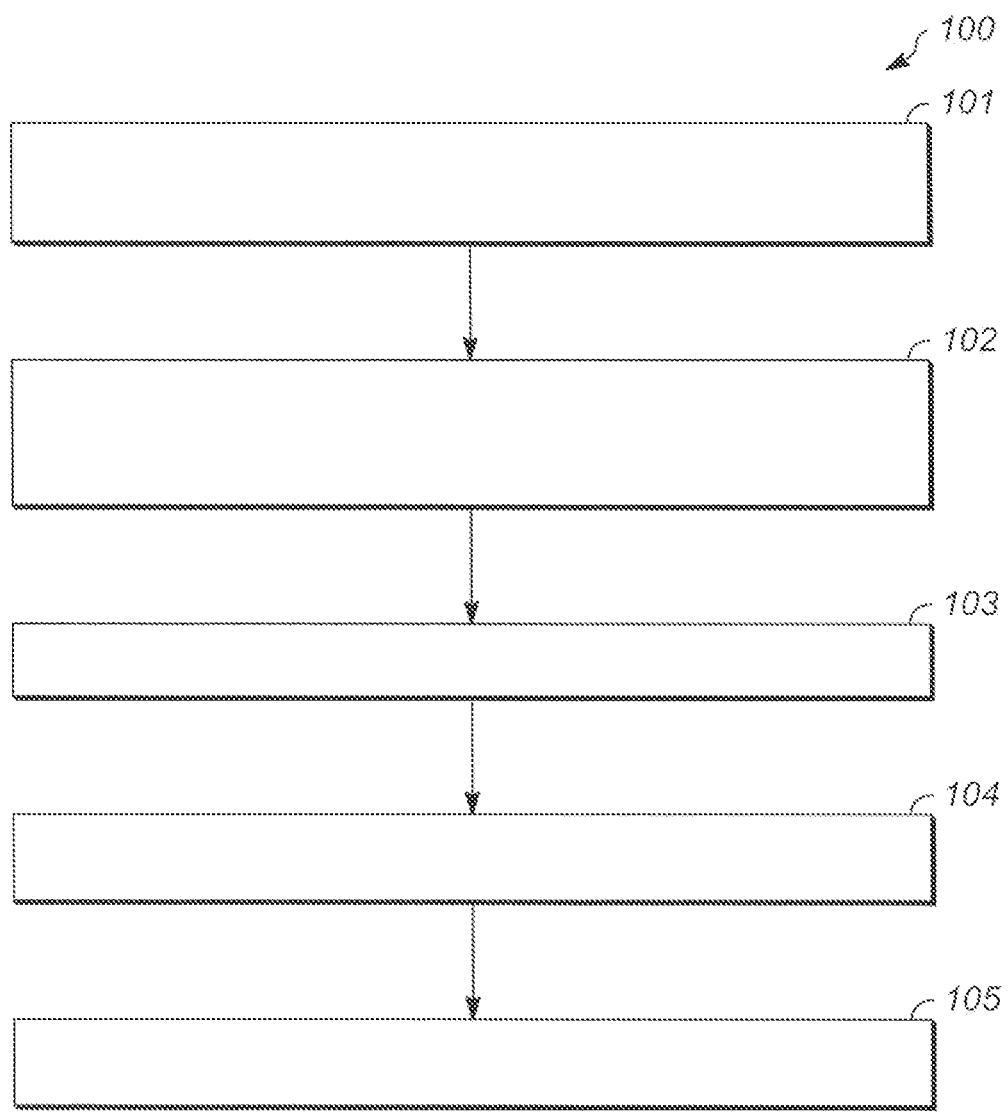
FIG. 1 is a simplified block diagram of a method for producing a zeolite catalyst in accordance with one exemplary embodiment.

With particular attention to FIG. 1, a typical method 100 includes combining or mixing (101) the zeolite (optionally milled) with a binder (or filler) material and a mulling step (102), where the zeolite particle is further reduced and dispersed into the binder uniformly. However, the force introduced to break up the zeolite aggregates also reduces the porosity of the catalyst due to the mechanical compaction. The reduced porosity adds diffusion resistance, lowering the utilization of the zeolite in the catalyst pellets. To attain good zeolite dispersion but alleviate the mechanical compaction, various organic additives are incorporated with optionally an increased amount of water into the preparation. Such an approach in general helps alleviate the compaction and gives reasonably high porosity, with minimal compaction introduced, but it is not useful in attaining an effective pore structures made up of interconnecting small and large pores.

It has been unexpectedly discovered, a zeolite preparation method 100 that achieves both uniform dispersion of the zeolite throughout the binder matrix and attains effective pore structures desired for delivering olefin throughout the catalyst: Specifically such characteristics are achieved by mulling a mixture of zeolite to reduce and disperse zeolite particles or optionally milled zeolite particle and gamma alumina particle instead of typical binders such as boehmite and pseudo-boehmite alumina, as has been typically performed in the art. In addition to gamma alumina other transition phase alumina such as chi, kappa, delta, eta, and theta can be used in place-ment of gamma alumina. In addition alpha alumina can be used in placement of gamma alumina as well.

Gamma and other transition alumina, and alpha alumina powders can be obtained commercially at varying particle size ranges with the particle size of less than 100 microns, more preferably less than 20 microns and most preferably less than 10 microns. The amount of alumina may range from about 10 weight % to about 80 weight % on a 100% solids basis, for example from about 20 weight % to about 40 weight %, such as about 30 weight %. The amount of zeolite should be an amount that effects sufficient catalytic activity to the ultimately produced catalyst for use in industrial hydrocarbon reactors. For example, the amount of zeolite may range from about 20 weight % to about 90 weight % on a 100% solids basis, for example from about 60 weight % to about 80 weight %, such as about 70 weight %.

In one embodiment the porosity enhancing agent may be incorporated as an organic agent or an inorganic agent. In an exemplary embodiment, the pore enhancing agent is an organic, water-insoluble agent, for example, a powdered cellulose fiber compound sold under the trade name SOLKA-FLOC® by the International Fiber Corporation of North Tonawanda, N.Y., USA. Another exemplary pororisty enhancing agent is tylose powder. In a further exemplary embodiment, the porosity enhancing agent is an organic, water-soluble agent, for example, a cellulose-derived polymer sold under the trade name Methocel® by the Dow Chemical Company of Midland, Mich., USA. The porosity enhancing agent may be provided to the extrudable mixture in an amount from about 2 weight % to about 10 weight % on a 100% solids basis, for example from about 4 weight % to about 8 weight %, such as about 4 or 6 weight %.

A sufficient amount of water should be added so that the mixture can be extruded into the desired catalyst shape. For example, the amount of water may be added so the content of the water ranges from about 30% to about 85% weight of the solids, for example, about 50 weight % to about 70 weight % of the solids. This extrudable mixture may be in the form of a dough.

As previously noted, methods for producing zeolite catalysts in accordance with the present disclosure may include a step of mulling the extrudable mixture. Mulling serves to disperse the zeolite particles within the dough mixture, which can increase diffusion within the catalyst. Typically mulling, however, can increase the density of the mixture by compacting the mixture, thereby limiting diffusion within the resulting catalyst. However, in the presently described exemplary method, mulling does not have such typical compaction effect most likely due to the replacement of boehmite alumina with gamma alumina in the catalyst formulation. As mentioned the resulting catalyst showed uniform zeolite dispersion, while attaining an effective pore structure, which is made up of small and large pores. Furthermore, the catalyst showed good physical strength.

The exemplary method 100 further includes extruding the mixture into a shaped catalyst (step 103). Various shapes are known in the art, for example generally spherical and generally cylindrical. It has been discovered that extruding the catalyst into a multi-lobed shape, for example a tri-lobed shape, increases the surface area of the catalyst for any given diameter, and therefore improves the reactants access to the catalyst active sites, which has been found to be particularly beneficial in diffusion-resistant applications. The circumference of an exemplary tri-lobe extruded catalyst shape ranges from about 0.1 inches to about 0.8 inches, for example from about 0.12 inches to about 0.7 inches, such as about 0.15 to about 0.55 inches. The diameter of such tri-lobe catalyst will range from about 0.1 inches to about 0.4 inches, for example about 0.120 to about 0.24 inches. The ratio of the length of the catalyst to its diameter can range from about 2:1 to about 4:1. The ratios of the external surface of the catalyst to its volume are greater than 80 $inch^{-1}$.

In an embodiment, the extrudate is dried and calcined (104), and then ammonium exchange to lower sodium contents (105). For example, the extrudate can be dried and calcined in a kiln at a temperature of from about 500° C. to about 700° C. for a time period of from about 20 minutes to about 90 minutes. The catalyst is thereafter washed in an aqueous, ammonium-containing bath to remove sodium after the calcination step. For example, the ammonium containing bath may include ammonium nitrate or ammonium sulfate at a temperature of from about 30° C. to about 100° C., for example about 60° C. The catalyst is washed for a time period of from about 0.5 hours to about 6 hours, for example about 2 hours. For an ammonium nitrate solution, an exemplary wash solution includes about 1 g of ammonium nitrate and about 5 to 10 grams of water per gram of catalyst. Other suitable washing bath compositions will be known to those having ordinary skill in the art.

Zeolite catalysts prepared in accordance with the foregoing exemplary method have been demonstrated to have a relatively high dispersion of zeolite particles in the catalyst binder matrix, thereby enhancing the amount of zeolite available to the reacting compounds. Furthermore, catalysts prepared in accordance with the foregoing exemplary method have been demonstrated to have a relatively high proportion of large-size pores, thereby improving the intra-particulate diffusion of the reacting compounds within the catalyst. Without being bound by theory, it is postulated that the improved dispersion of zeolite particles is due to the use of a binder material with a different morphology than the zeolite. For example, certain zeolite such as UZM-8 zeolite has a "plate-like" morphology. Thus, using a binder that also has a plate-like morphology, such as un-treated boehmite, would favor plate "stacking" or densification of the mixture. In contrast, according to the methods presented herein, the boehmite may be calcined to form gamma alumina, which has sintered to a large particles with a shape that differs from the plate-like zeolite. As such, when using gamma alumina, densification caused by the stacking of plate zeolite and boehmite alumina is minimized. The outcome is a porous catalyst with well disperse zeolite and effective pore structure and thus enhanced diffusion properties.

The following are exemplary embodiments of zeolite catalysts as contemplated herein. The examples are provided for illustrative purposes only and are not meant to limit the various embodiments of the methods for producing zeolite catalysts in any way.

EXAMPLES

Five exemplary catalysts, Examples 1-5 in Table 1, above, were prepared as follows. Catalyst Examples 1, 2, and 3 were prepared in accordance with the exemplary method set forth above. Catalyst Examples 4 and 5 were prepared using previously known methods as a reference comparison. With regard to each of Examples 1-5, a zeolite stock of UZM-8 material was milled using a single-pass milling procedure to produce a particle distribution having at least 80% of the particles in the range of about 10 microns to about 100 microns. The milled zeolite was mixed with an alumina filler material that acted as a binder, at a ratio of about 70:30 zeolite to alumina. In Examples 1-3, gamma alumina was used, which, as discussed above, results in a greater dispersion of zeolite catalyst due to the difference in shape between the zeolite particles and the gamma alumina particles. In Examples 4-5, beohmite was used, which, as discussed above, has a plate-like shape similar to milled zeolite. A pore enhancing agent was then added to each mixture. In Examples 1-3, 4% by weight of solids Methocel® was used. In example 4, 6% by weight solids SOLKA-FLOC® was used. In Example 5, 6% by weight of solids tylose was used. A sufficient amount of water was added, in an amount of about 65% by weight of the solids to form an extrudable paste or dough. The mixture was mulled in Examples 1-3, but the mixture was not mulled in Examples 4-5. The paste was then extruded through a tri-lobe shaped die in all but Example 1, where a cylinder shape was used. Thereafter, the extruded catalyst was dried, calcined, and washed in aqueous ammonium in accordance with the exemplary method set forth above.

Figure 2:
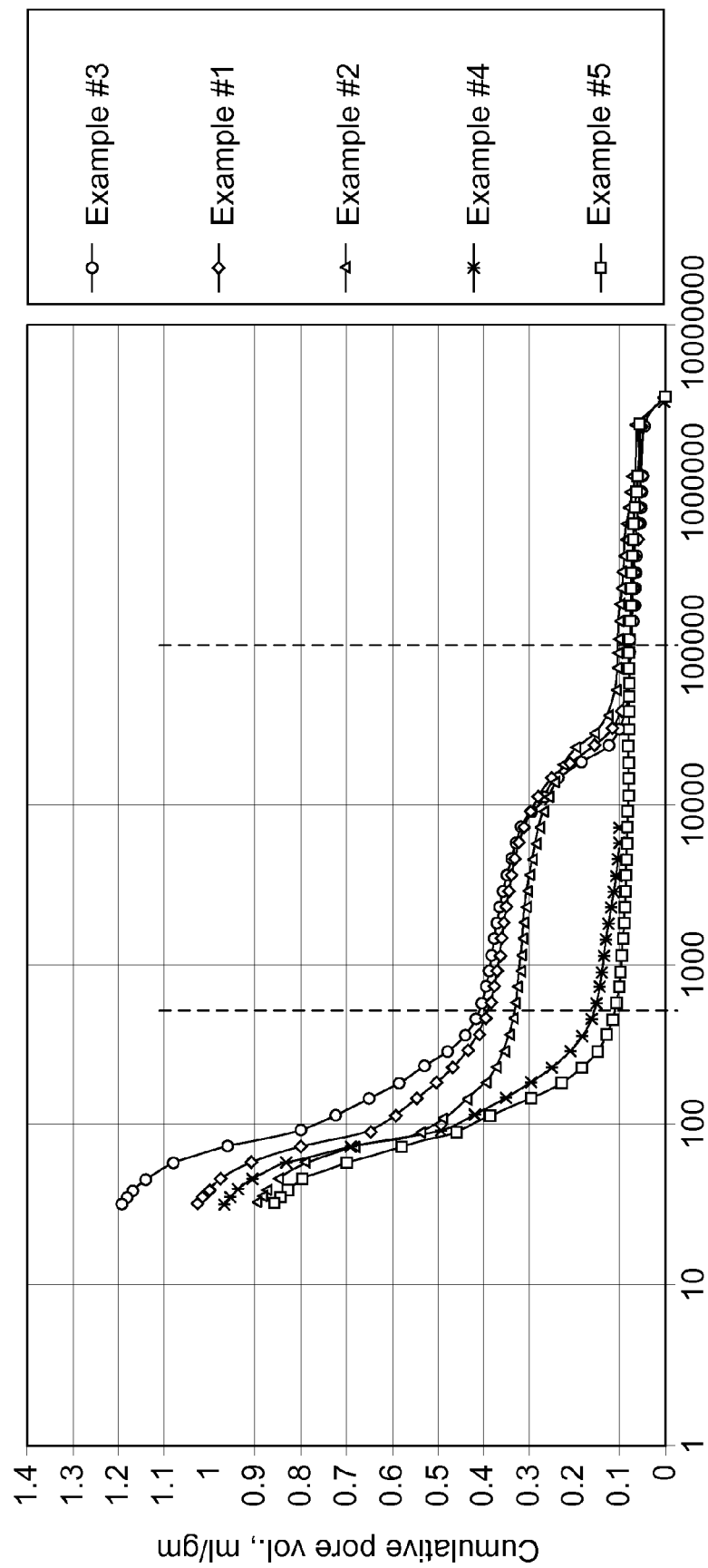
FIG. 2 depicts the pore size distribution of exemplary catalysts produced in accordance with the method shown in FIG. 1.

The catalysts of Examples 1-5 were then analyzed to determine pore size distribution using known mercury penetration techniques. FIG. 2 shows the cumulative pore size distribution for catalyst Examples 1-5. (Data regarding the total pore volume of each exemplary catalyst, along with the pore volume in the pore size range of about 600 Å to about 31000 Å (large pores), is also provided above in Table 1.) As can be seen, the catalysts prepared in accordance with the exemplary method (Examples 1-3) exhibit significantly higher porosity in the range from about 600 Å (indicated by first dashed line) to about 31,000 Å (indicated by second dashed line) diameter, and have a greater percentage of total pores in this range. In particular, the catalysts prepared in accordance with the exemplary method exhibited a total porosity by Hg intrusion of greater than about 0.60 ml/gm and greater than 15% of a total pore volume in the range from about 550 Å to about 31,000 Å.

Figure 3:
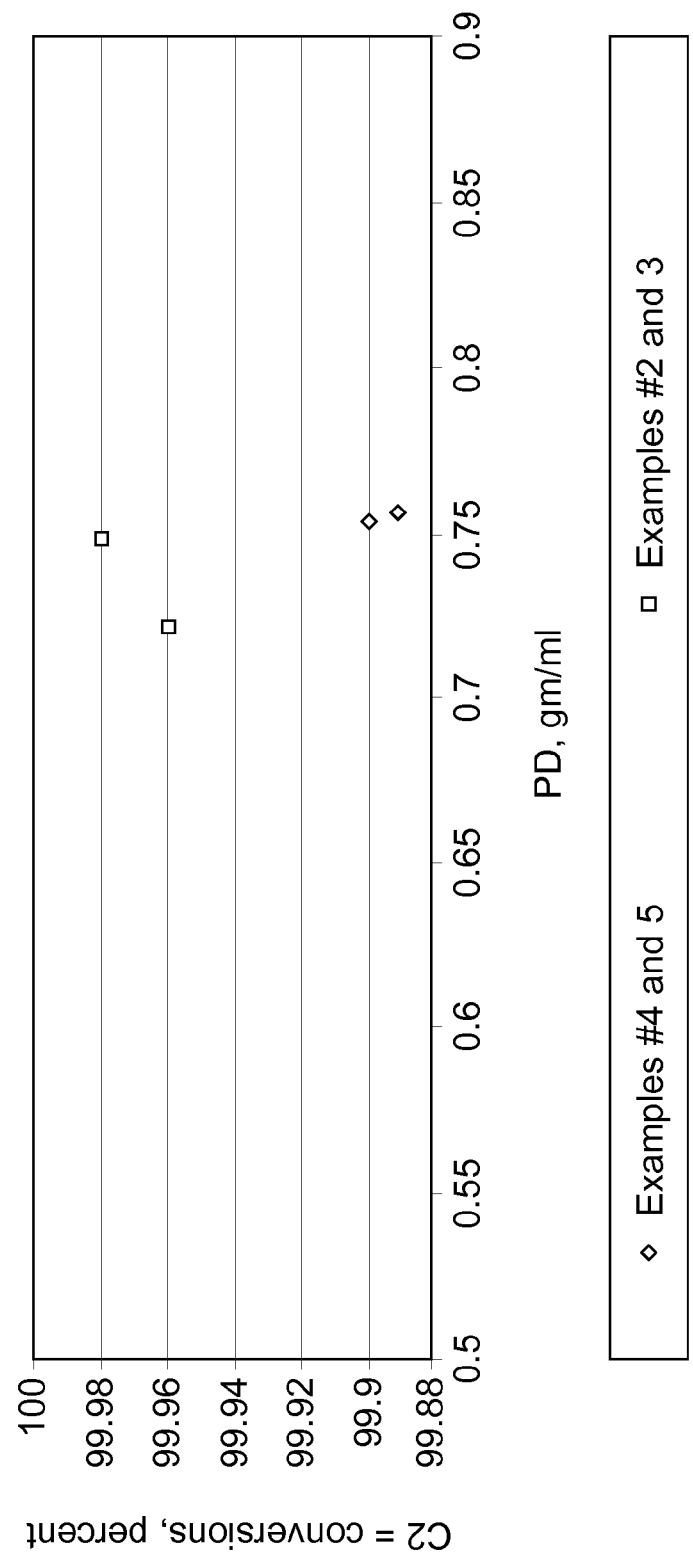
FIG. 3 depicts the percentage of ethylene converted in an alkylation reaction of ethylene and benzene using exemplary catalysts produced in accordance with the method shown in FIG. 1.

The catalysts of Examples 2-5 were then employed in a test-scale reactor for alkylating benzene with ethylene. The reaction was run at a temperature of about 215° C. inlet, at a benzene to olefin molar ratio of about 20, and at a pressure of about 550 psig. As shown in FIG. 3, the catalysts prepared in accordance with the exemplary method (Examples 2 and 3 (Example 1 having not been tested)) displayed a higher olefin

TABLE 1

| Ex # | Shape | Pore Enhancer/ Binder | Mulled | Density, gm/ml | Total Pore Volume, ml/gm | Pore Volume (600-31000 Å diameter), ml/gm | % of Pores in (600-31000 Å diameter) |
|---|---|---|---|---|---|---|---|
| 1 | Cylinder | 4% Methocel/ Gamma Alumina | Yes | 0.668 | 1.024 | 0.258 | 25.2 |
| 2 | Trilobe | 4% Methocel/ Gamma Alumina | Yes | 0.749 | 0.899 | 0.242 | 26.9 |
| 3 | Trilobe | 4% Methocel/ Gamma Alumina | Yes | 0.722 | 1.191 | 0.311 | 26.1 |
| 4 | Trilobe | 6% Solka Floc/ Boehmite | No | 0.754 | 0.965 | 0.072 | 7.5 |
| 5 | Trilobe | 6% Tylose/ Boehmite | No | 0.757 | 0.857 | 0.031 | 3.6 | conversion. The results demonstrate the benefit of high total porosity and high proportion of pores in the range from about 600 Å to about 31,000 Å diameter.

Figure 4:
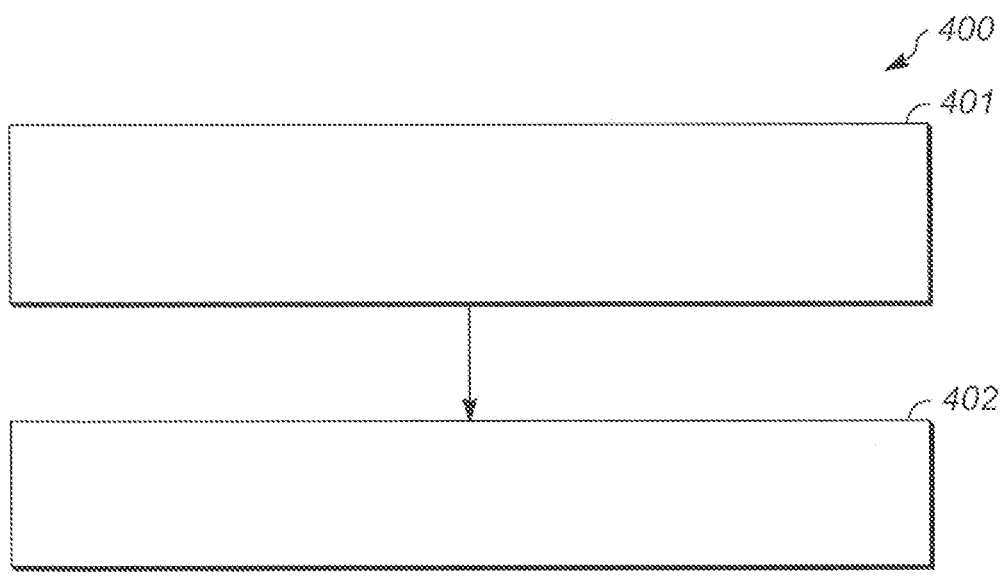
FIG. 4 is a simplified block diagram of a method for producing an alkylated benzene compound in accordance with one exemplary embodiment.

A method 400 for producing alkylated benzene compound using the zeolite catalysts as described above, in accordance with an exemplary embodiment, is described with reference to FIG. 4. The method includes providing a zeolite catalyst (step 401). The zeolite catalyst can be formed using any of the various embodiments for making zeolite catalysts as described above. For example, in one embodiment, the zeolite catalyst is formed from a mixture including a zeolite stock material, a gamma alumina filler, a porosity enhancing agent, and water. The method further includes contacting a hydrocarbon stream comprising benzene and an olefin in the presence of the zeolite catalyst.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the processes without departing from the scope defined by the claims, which includes known equivalents and foreseeable equivalents at the time of this disclosure.

What is claimed is:

1. A method for producing an alkylated benzene compound comprising:
    mixing a UZM-8 zeolite material with a filler material comprising transition phase alumina including Chi, Kappa, Delta, Eta, Theta, and Gamma, and an Alpha alumina, a porosity enhancing agent, and water to produce a paste;
    mulling the paste;
    extruding the paste to produce a shaped extrudate;
    drying and calcining the shaped extrudate to produce a zeolite catalyst, wherein the zeolite catalyst has a total porosity greater than about 0.60 ml/gm and greater than 15% of a total pore volume of pores in the range from about 550 angstroms to about 31,000 angstroms; and
    contacting a hydrocarbon stream comprising benzene and an olefin in the presence of the zeolite catalyst.

2. The method of claim 1, wherein contacting the hydrocarbon stream comprising ethylene or propylene.

3. The method of claim 1, wherein contacting the hydrocarbon stream comprises contacting a hydrocarbon stream having a benzene:olefin ratio in the range from about 1.0 to about 20, preferably from about 1.5 to about 10.

4. The method of claim 1, wherein contacting the hydrocarbon stream comprises contacting a hydrocarbon stream having a benzene to olefin ratio in the range from about 1.0 to about 20, or from about 1.5 to about 10, and in temperature range from 100 to 260° C., or from about 150 to about 250° C.

5. The method of claim 1, wherein contacting the hydrocarbon stream comprises contacting the hydrocarbon stream in the presence of a tri-lobed zeolite catalyst.

6. The method of claim 1, wherein milling the stock zeolite material comprises milling the stock zeolite material to produce a milled zeolite having an average particle size distribution in the range from about 10 microns to about 100 microns.

7. The method of claim 1, wherein mixing the zeolite with a pore enhancing agent comprises mixing the zeolite with an organic, water-soluble porosity enhancing agent, an organic water insoluble porosity enhancing agent, or a mixture of thereof.

8. The method of claim 1, wherein the mixture comprising the zeolite, transition phase or alpha alumina and porosity enhancing agents is mulled over a period of time from about 10 to about 360 minutes.

9. The method of claim 1, wherein calcining the shaped extrudate comprises calcining at a temperature from about 500° C. to about 700° C. for a time period from about 20 minutes to about 240 minutes.

10. The method of claim 1, wherein the olefin is ethylene.

11. The method of claim 1, wherein the transition phase alumina and alpha alumina have a particle size of less than 100 microns.

12. The method of claim 1, wherein the transition phase alumina and alpha alumina have a particle size of less than 20 microns.

13. The method of claim 1, wherein the transition phase alumina and alpha alumina have a particle size of less than 10 microns.

14. The method of claim 1, wherein the porosity enhancing agent comprises from about 2 wt. % to about 10 wt. % of the solids of the paste.

15. The method of claim 1, wherein the porosity enhancing agent comprises from about 4 wt. % to about 8 wt. % of the solids of the paste.

16. The method of claim1, wherein the porosity enhancing agent comprises from about 4 wt. % to about 6 wt. % of the solids of the paste.

* * * * *